(12) United States Patent
Sakagawa

(10) Patent No.: US 8,132,914 B2
(45) Date of Patent: Mar. 13, 2012

(54) IMAGING CONTROL APPARATUS FOR CAPTURING TOMOGRAM OF FUNDUS, IMAGING APPARATUS, IMAGING CONTROL METHOD, PROGRAM, AND STORAGE MEDIUM

(75) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/759,622

(22) Filed: Apr. 13, 2010

(65) Prior Publication Data

US 2010/0195050 A1 Aug. 5, 2010

Related U.S. Application Data

(63) Continuation of application No. PCT/JP2009/004360, filed on Sep. 3, 2009.

(30) Foreign Application Priority Data

Oct. 21, 2008 (JP) .................................. 2008-271439

(51) Int. Cl.
*A61B 3/14* (2006.01)
(52) U.S. Cl. ......................... 351/208; 351/209; 351/206
(58) Field of Classification Search .................. 351/209, 351/205, 206, 204, 208, 210, 246
See application file for complete search history.

(56) References Cited

U.S. PATENT DOCUMENTS

| 5,640,963 | A | 6/1997 | Tanaka | |
|---|---|---|---|---|
| 5,712,474 | A | 1/1998 | Kaneda | |
| 6,325,512 | B1* | 12/2001 | Wei | 351/209 |
| 7,510,282 | B2 | 3/2009 | Ueno et al. | |
| 7,566,128 | B2 | 7/2009 | Tsukada | |
| 2004/0036838 | A1* | 2/2004 | Podoleanu et al. | 351/206 |
| 2006/0228011 | A1* | 10/2006 | Everett et al. | 382/128 |
| 2007/0070295 | A1* | 3/2007 | Tsukada et al. | 351/206 |
| 2007/0222945 | A1* | 9/2007 | Tsukada et al. | 351/205 |
| 2007/0222946 | A1* | 9/2007 | Fukuma et al. | 351/206 |
| 2008/0151260 | A1* | 6/2008 | Kikawa et al. | 356/521 |
| 2008/0259275 | A1* | 10/2008 | Aoki et al. | 351/210 |
| 2009/0027685 | A1* | 1/2009 | Abe et al. | 356/477 |
| 2009/0161826 | A1* | 6/2009 | Gertner et al. | 378/65 |

(Continued)

FOREIGN PATENT DOCUMENTS

JP H06-503733 T 4/1994

(Continued)

OTHER PUBLICATIONS

Krahmer, F. et al, "Blind Image Deconvolution: Motion Blur Estimation", Aug. 18, 2006, pp. 1-14.

(Continued)

*Primary Examiner* — Mohammed Hasan
(74) *Attorney, Agent, or Firm* — Canon U.S.A., Inc., IP Division

(57) ABSTRACT

An imaging control apparatus which controls an imaging unit configured to capture a tomogram of the fundus of a target eye includes an acquisition unit configured to acquire information representing the direction of a fundus movement of the target eye, an analysis unit configured to analyze the direction of the fundus movement based on the information acquired by the acquisition unit, and a control unit configured to control the imaging unit so as to align the direction of imaging of the imaging unit with the direction of the fundus movement based on the analysis result of the analysis unit.

18 Claims, 13 Drawing Sheets

U.S. PATENT DOCUMENTS

| | | | |
|---|---|---|---|
| 2010/0053553 A1* | 3/2010 | Zinser | 351/206 |
| 2010/0149489 A1* | 6/2010 | Kikawa et al. | 351/206 |

FOREIGN PATENT DOCUMENTS

| | | |
|---|---|---|
| JP | H07-107368 A | 4/1995 |
| JP | H07-155299 A | 6/1995 |
| JP | H09-140671 A | 6/1997 |
| JP | 2007-117714 A | 5/2007 |
| JP | 2007-130403 A | 5/2007 |
| JP | 2008-029467 A | 2/2008 |
| WO | 92/03084 A | 3/1992 |
| WO | 02/35996 A | 5/2002 |
| WO | WO2008/052793 * | 5/2008 |

OTHER PUBLICATIONS

Moghaddam, M.E. et al, "Linear motion blur parameter estimation in noisy images using fuzzy sets and power spectrum", EURASIP Journal on Advances in Signal Processing, vol. 2007, Article ID 68985, 8 pages.

* cited by examiner

F I G. 4
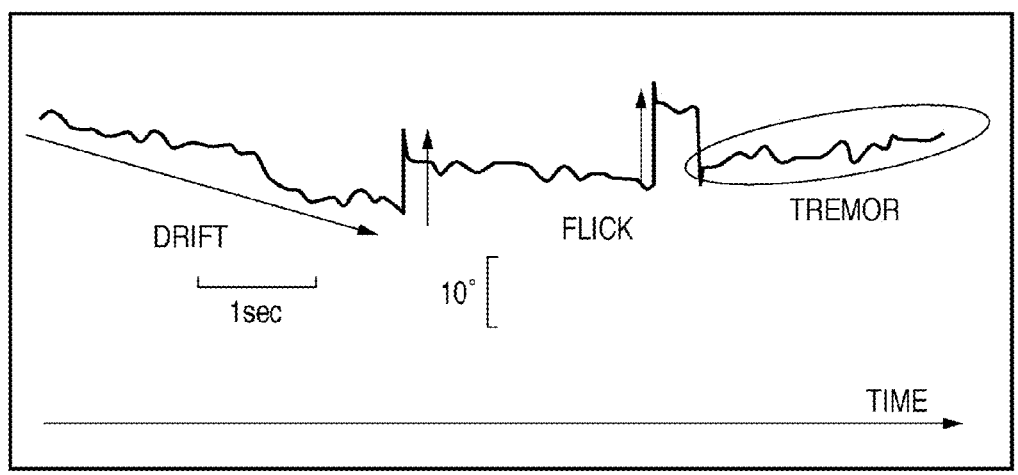

F I G. 10
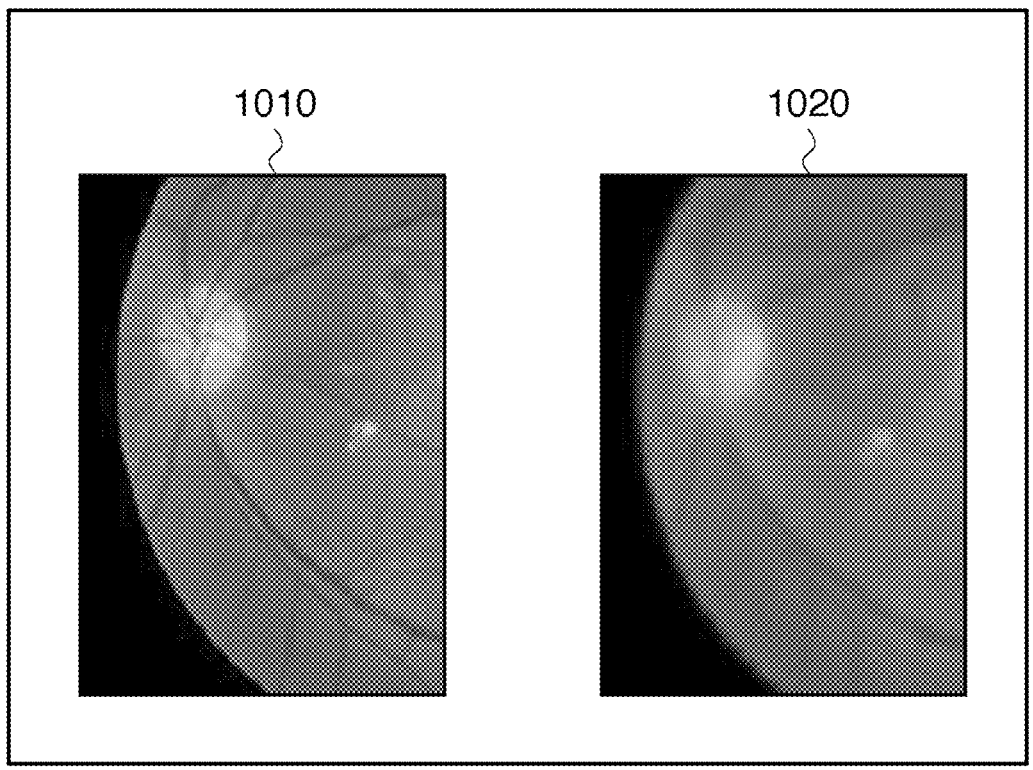

IMAGING CONTROL APPARATUS FOR CAPTURING TOMOGRAM OF FUNDUS, IMAGING APPARATUS, IMAGING CONTROL METHOD, PROGRAM, AND STORAGE MEDIUM

CROSS REFERENCE

This application is a continuation of International Application No. PCT/JP2009/004360, filed Sep. 3, 2009, which claims the benefit of Japanese Patent Application No. 2008-271439, filed Oct. 21, 2008, both of which are hereby incorporated by reference in their entireties.

TECHNICAL FIELD

The present invention relates to an imaging control apparatus, imaging apparatus, imaging control method, program, and storage medium.

BACKGROUND ART

Eye examinations are widely made for the purpose of early diagnosis of life-related diseases or various diseases that are leading causes of blindness. In the examinations and the like, it is necessary to find diseases all over the eye. For this reason, an examination using an image (to be referred to as a broad image hereinafter) in a broader range of an eye is essential. A broad image is obtained using, for example, a fundus camera or an SLO (Scanning Laser Opthalmoscope).

On the other hand, an eye tomogram acquisition apparatus of an OCT (Optical Coherence Tomography) or the like can quantify a disease state based on an objective measure and is therefore expected to be useful for more reliably diagnosing diseases. In a general OCT, an operator decides the tomogram imaging parameters (for example, target part, imaging range, precision level, scanning method, and the like), and images and analyzes only a local eye region based on the imaging parameters.

As a technique of assisting operator's tomographic imaging, for example, patent reference 1 discloses a technique concerning a user interface for designating the tomographic imaging range of an OCT on a broad image obtained by a fundus camera. Patent reference 2 discloses a technique concerning a user interface for designating the tomographic imaging range of an OCT on a broad image obtained by an SLO. According to patent reference 1 or 2, the imaging parameters can be set relatively easily because it is possible to decide the tomographic imaging range while referring to the state of a broad fundus image.

However, the human eye is constantly in an unconscious feeble motion called a small involuntary eye movement even when gazing at a fixed point. The small involuntary eye movement is known to mainly contain three components (feeble motion components) (see FIG. 4).

(1) Tremor: a frequency component of 30 to 100 Hz at a visual angle of about 50°.

(2) Flick: a step- or pulse-like movement which occurs without periodicity (at an interval of about 0.03 to 5 sec) at a visual angle of about 20°.

(3) Drift: a slow movement which exists between flicks at a visual angle of about 10'.

During the measurement processing time of the OCT, a measurement light beam needs to accurately strike a measurement part. Actually, it is difficult to continuously accurately apply a measurement light beam to a measurement part because of, for example, the small involuntary eye movement of the target eye.

Each of patent references 3 and 4 discloses an apparatus which includes a tracking means for moving the irradiation position of a measurement light beam onto a measurement part in real time in correspondence with a small involuntary eye movement.

PRIOR ART REFERENCES

Patent References

Patent reference 1: Japanese Patent Laid-Open No. 2007-117714
Patent reference 2: Japanese Patent Laid-Open No. 2008-029467
Patent reference 3: Japanese Patent Laid-Open No. 6-503733
Patent reference 4: Japanese Patent Laid-Open No. 7-155299

Non-Patent References

Non-patent reference 1: Koji Imao et al.: "Estimation of Motion Direction from Motion Blur in Image Sequence", Proceedings of the IEICE General Conference, Vol. 1997 No. 2
Non-patent reference 2: Krahmer, F. et al.: "Blind Image Deconvolution: Motion Blur Estimation", 2006
Non-patent reference 3: Moghaddam, M. E. et al.: "Linear motion blur parameter estimation in noisy images using fuzzy sets and power spectrum", EURASIP Journal on Advances in Signal Processing, 2007

PROBLEMS THAT THE INVENTION IS TO SOLVE

When manually designating imaging parameters for tomographic imaging, the state of a small involuntary eye movement of the target eye immediately before imaging may be unknown, and the influence of a small involuntary eye movement may be suppressed by shortening the measurement time. In this case, the number of measurement points (sampling points) is also decreased. It is therefore not easy to appropriately set such imaging parameters that minimize the influence of a small involuntary eye movement.

Use of the technique of patent reference 3 or 4 allows to suppress the influence of a small involuntary eye movement by correcting OCT imaging while detecting the small involuntary eye movement. In this case, imaging is done based on a preset traversal scan speed and direction. Hence, the traversal scan speed and direction for imaging are not set in accordance with the characteristics of the small involuntary eye movement of each target eye upon imaging. An apparatus having the tracking function becomes complex because it needs to emit the measurement beam and the tracking beam simultaneously.

SUMMARY OF THE INVENTION

The present invention has been made in consideration of the above-described problems, and has as its object to provide an imaging control technique capable of suppressing the influence of an eye movement in tomographic fundus imaging.

According to one aspect of the present invention, there is provided an imaging control apparatus which controls an imaging unit adapted to capture a tomogram of a fundus of a target eye, comprising:

an acquisition unit adapted to acquire information representing a direction of a fundus movement of the target eye;

an analysis unit adapted to analyze the direction of the fundus movement based on the information acquired by the acquisition unit; and a control unit adapted to control the imaging unit so as to align a direction of imaging of the imaging unit with the direction of the fundus movement based on an analysis result of the analysis unit.

According to the present invention, it is possible to provide an imaging control technique capable of suppressing the influence of an eye movement in tomographic fundus imaging.

Further features and advantages of the present invention will become apparent from the following description with reference to the accompanying drawings. Note that the same reference numerals denote the same or similar parts throughout the accompanying drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 4 is a view showing three components of a small involuntary eye movement that is a fundus movement;

FIG. 10 is a view showing an example of a broad image according to the first embodiment;

DESCRIPTION OF THE INVENTION

Preferred embodiments of the present invention will now be described in detail with reference to the accompanying drawings. Note that the constituent elements described in the embodiments are merely examples. The technical scope of the present invention is determined by the scope of claims and is not limited by the following individual embodiments.

First Embodiment

Figure 1:
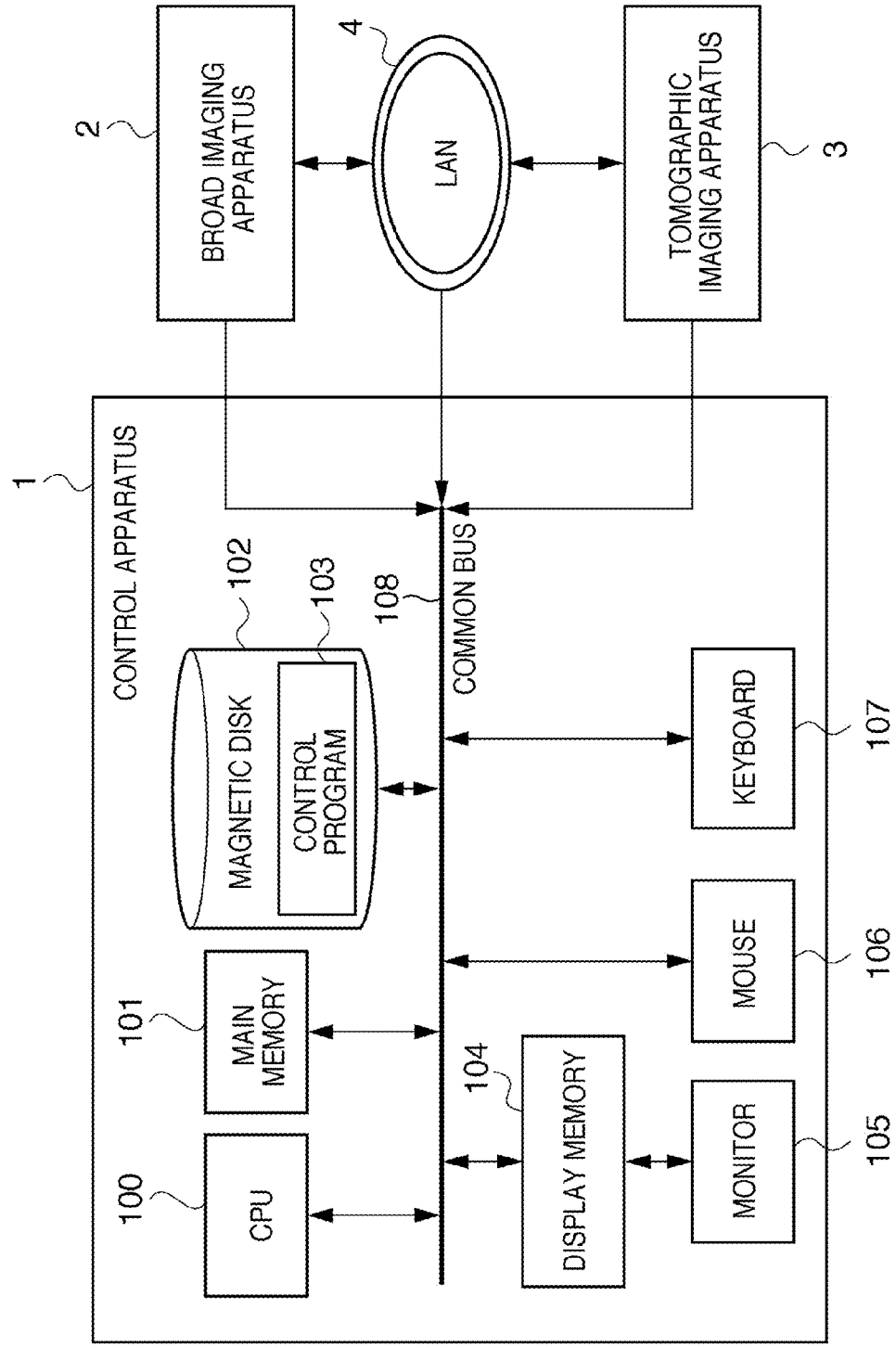
FIG. 1 is a block diagram showing the arrangement of a control apparatus 1 of a tomographic fundus imaging apparatus according to the first embodiment.

The arrangement of the embodiment will be explained first. FIG. 1 is a block diagram schematically showing the apparatus arrangement of a diagnostic system according to an embodiment of the present invention. A tomographic fundus imaging apparatus for capturing a tomogram of the fundus of a target eye includes a control apparatus 1. The control apparatus 1 includes a central processing unit (CPU) 100, main memory 101, magnetic disk 102, control program 103, display memory 104, monitor 105, mouse 106, keyboard 107, and common bus 108.

The central processing unit (CPU) 100 mainly controls the operation of each constituent element of the control apparatus 1 (imaging control apparatus). The main memory 101 can store an apparatus control program and function as a work area for program execution. The magnetic disk 102 stores an operating system (OS), the device drives of peripheral devices, the control program 103 (to be also simply referred to as a "program" hereinafter) to be used to perform various kinds of processes to be described later, and the like. The display memory 104 can temporarily store display data. The monitor 105 is, for example, a CRT monitor or a liquid crystal monitor and displays an image based on data from the display memory 104. The mouse 106 and the keyboard 107 are used for pointing input and input of characters and the like by the user, respectively. The common bus 108 connects the above-described constituent elements to each other.

As shown in FIG. 1, the control apparatus 1 of the tomographic fundus imaging apparatus (imaging apparatus) is connected to a broad imaging apparatus 2 and a tomographic imaging apparatus 3 via a local area network (LAN) 4 such as Ethernet. Note that the devices may be connected via an external interface such as a USB or IEEE1394.

The broad imaging apparatus 2 captures a broad image of an eye and includes, for example, a fundus camera or an SLO (Scanning Laser Opthalmoscope).

Figure 5:
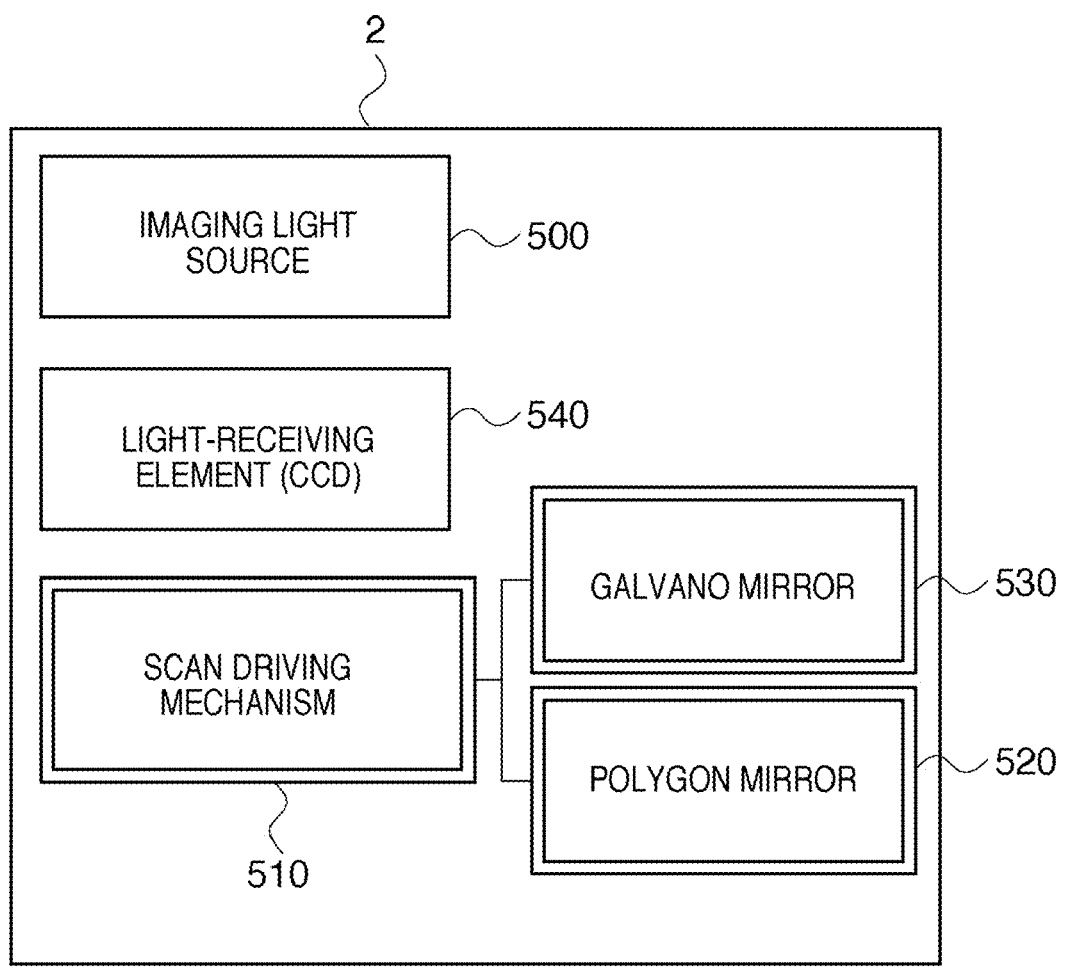
FIG. 5 is a block diagram showing the functional arrangement of a broad imaging apparatus 2 according to the first embodiment.

FIG. 5 illustrates the functional arrangement of the broad imaging apparatus 2 formed from an SLO. As shown in FIG. 5, to capture a broad eye image, the broad imaging apparatus 2 controls a polygon mirror 520 and a galvano mirror 530 via a scan driving mechanism 510. A light-receiving element 540 formed from, for example, a CCD receives the reflected light of a weak laser beam emitted from an imaging light source 500, thereby capturing g a broad eye image. Note that the device arrangement and driving mechanism control of the SLO are described in detail in patent reference 2. In this embodiment, an example will be described in which an image from a fundus camera serving as the broad imaging apparatus is used. The device arrangement and driving mechanism control of the fundus camera are described in detail in patent reference 1.

Figure 6:
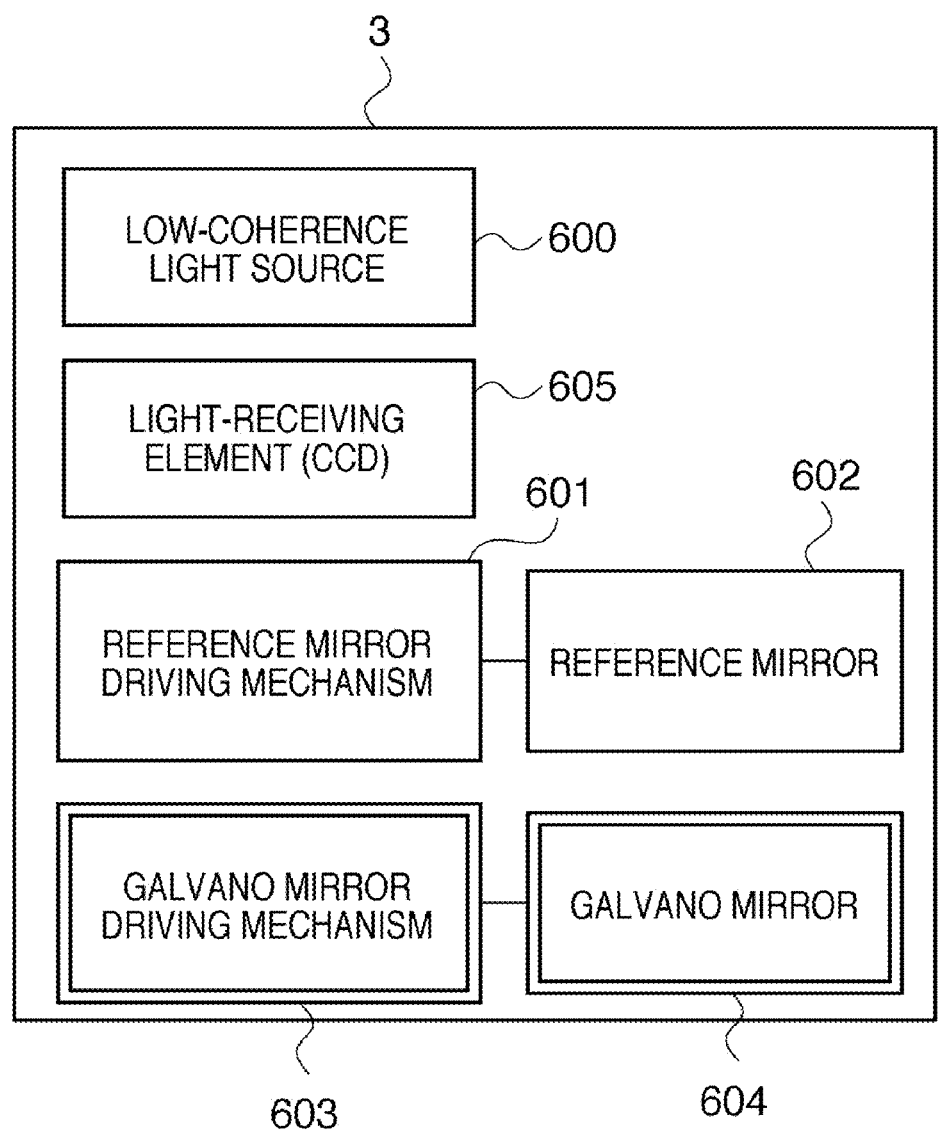
FIG. 6 is a block diagram showing the functional arrangement of a tomographic imaging apparatus 3 according to the first embodiment.

The tomographic imaging apparatus 3 captures a tomogram of an eye and includes, for example, an OCT (Optical Coherence Tomography) of time domain scheme or an OCT of Fourier domain scheme. FIG. 6 illustrates the functional arrangement of the tomographic imaging apparatus 3 formed from an OCT of time domain scheme. The tomographic imaging apparatus 3 receives parameters for designating imaging contents from the control apparatus 1 of the tomographic fundus imaging apparatus and executes tomographic imaging using the received parameters. The obtained tomogram is output to the control apparatus 1 of the tomographic fundus imaging apparatus.

Figure 7:
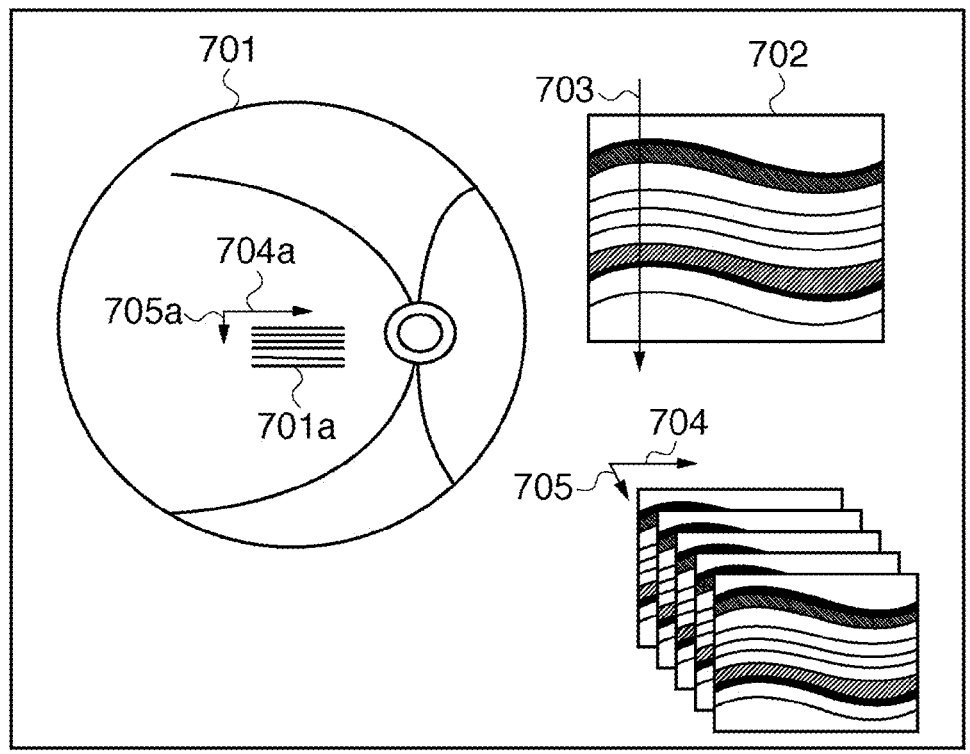
FIG. 7 is a view for explaining a scan movement in tomographic imaging.

The parameters for designating imaging contents designate a scanning method including a tomogram acquisition part and position, the spatial range of a tomogram, a precision level such as a scan line (A scan) interval, a traversal scan order, a scan direction, and a scan speed. FIG. 7 shows an example of a fundus image 701 obtained from the broad imaging apparatus 2 and an example of a retinal tomogram 702 obtained from the tomographic imaging apparatus 3. Reference numeral 701a indicates a position of the tomogram 702. In the example of FIG. 7, the tomogram 702 is formed from a plurality of scan lines (also called A scans) 703 that scan in the depth direction of the retina. The scan lines travel on the retina to form one tomogram. Reference numerals 704 and 704a indicate traveling of the scan lines. The traveling is also called traversal scan or main scan. When continuously capturing tomograms, the imaging traveling is represented by 705 or 705a. This traveling is also called sub-scan.

The tomographic imaging apparatus 3 controls a reference mirror driving mechanism 601 and a galvano mirror driving mechanism 603 in accordance with the parameters to drive a reference mirror 602 and a galvano mirror 604. A light-receiving element 605 formed from, for example, a CCD receives the reflected light of light emitted from a low-coherence light source 600, thereby capturing an eye tomogram. Note that if the tomographic imaging apparatus 3 is formed from an OCT of Fourier domain scheme, only the galvano mirror 604 is controlled. Note that the device arrangement and driving mechanism control of the OCT are described in detail in patent reference 1 or 2.

Figure 2:
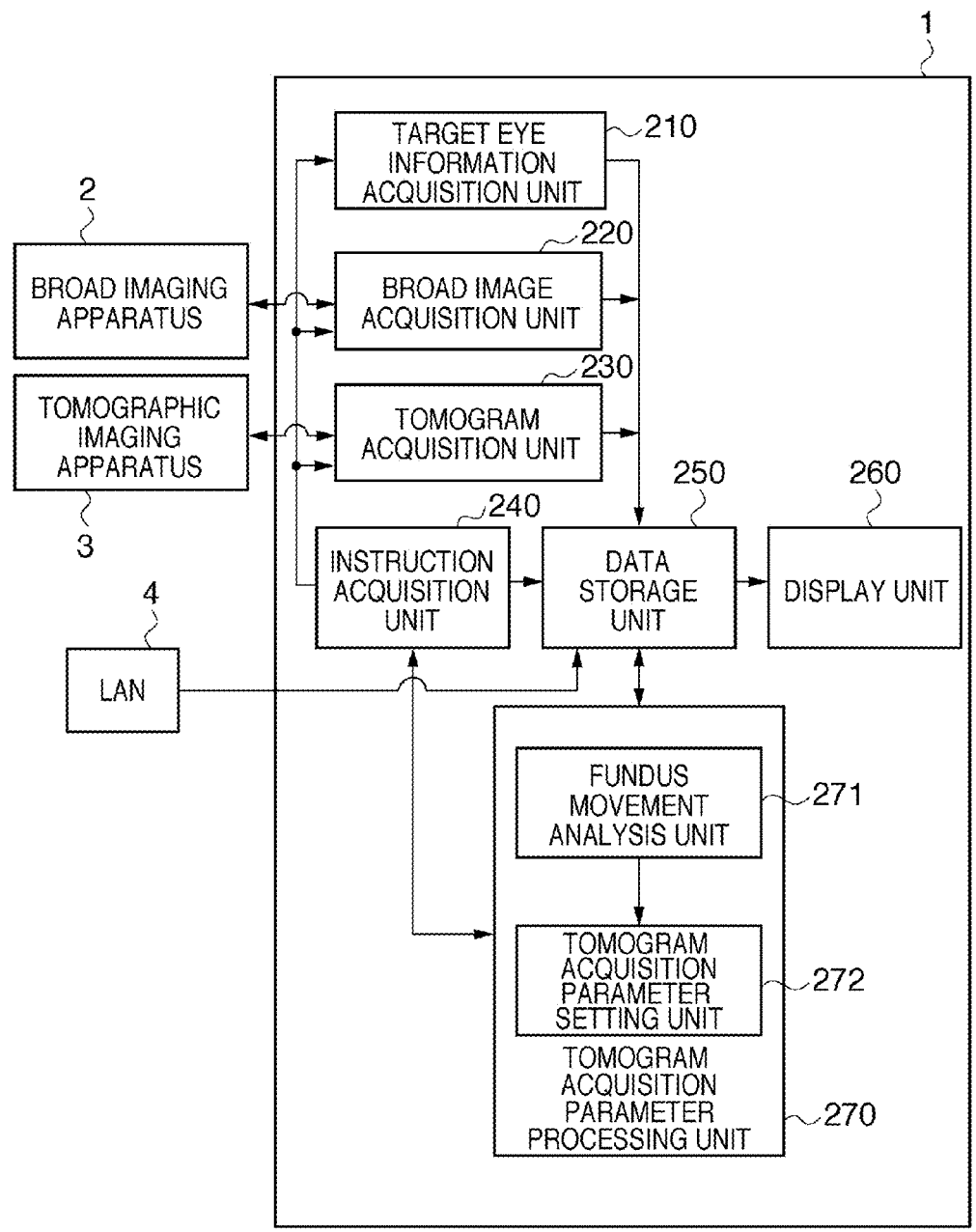
FIG. 2 is a block diagram showing the functional arrangement of the control apparatus 1 of the tomographic fundus imaging apparatus according to the first embodiment.

The functional arrangement of the control apparatus 1 of the tomographic fundus imaging apparatus will be described next with reference to FIG. 2. FIG. 2 is a functional block diagram of the control apparatus 1 of the tomographic fundus imaging apparatus according to the embodiment. As shown in FIG. 2, the control apparatus 1 of the tomographic fundus imaging apparatus includes a target eye information acquisition unit 210, broad image acquisition unit 220, tomogram acquisition unit 230, instruction acquisition unit 240, data storage unit 250, display unit 260, and tomogram acquisition parameter processing unit 270.

(Target Eye Information Acquisition Unit 210)

The target eye information acquisition unit 210 externally acquires information to identify a target eye. Information to identify a target eye is, for example, an identification number assigned to each target eye. Otherwise, the identification number of the target eye and an identifier representing whether the target eye is a right eye or left eye may be combined and used as the information to identify a target eye. The information also contains ecological information such as the age and medical record of the patient.

The operator inputs the information to identify the target eye. Note that when the tomographic imaging apparatus 3 holds the information to identify the target eye, the information may be acquired from the tomographic imaging apparatus 3 together with a tomogram. Based on the information to identify the target eye, the target eye information acquisition unit 210 also acquires information about the target eye held in the magnetic disk 102.

(Instruction Acquisition Unit 240)

The instruction acquisition unit 240 functions as a setting means for receiving imaging parameter settings to obtain a fundus tomogram. The instruction acquisition unit 240 acquires a process instruction that the operator inputs using the mouse 106 or the keyboard 107. For example, the instruction acquisition unit 240 acquires imaging parameters such as a fundus tomogram imaging position and imaging range to obtain a fundus tomogram. Alternatively, the instruction acquisition unit 240 acquires an imaging start instruction, initial parameters of tomogram acquisition parameters, an instruction to designate whether to store a captured tomogram, an instruction of a storage location, and the like. The instruction acquisition unit 240 transmits the contents of acquired instructions to the broad image acquisition unit 220, tomogram acquisition unit 230, data storage unit 250, display unit 260, and tomogram acquisition parameter processing unit 270 as needed.

(Broad Image Acquisition Unit 220)

Based on an instruction acquired by the instruction acquisition unit 240, the broad image acquisition unit 220 requests the broad imaging apparatus 2 to capture and transmit a broad image and acquires a broad eye image transmitted from the broad imaging apparatus 2. The broad image acquisition unit 220 transmits the acquired broad image to the tomogram acquisition parameter processing unit 270, display unit 260, and data storage unit 250.

(Tomogram Acquisition Unit 230)

Based on an instruction acquired by the instruction acquisition unit 240, the tomogram acquisition unit 230 transmits a tomographic imaging request to the tomographic imaging apparatus 3 together with parameters set by a tomogram acquisition parameter setting unit 272 to designate imaging contents. The tomogram acquisition unit 230 then acquires a tomogram transmitted from the tomographic imaging apparatus 3. The tomogram acquisition unit 230 transmits the acquired tomogram to the display unit 260 and the data storage unit 250.

(Tomogram Acquisition Parameter Processing Unit 270)

The tomogram acquisition parameter processing unit 270 includes a fundus movement analysis unit 271 and the tomogram acquisition parameter setting unit 272. Imaging parameters set by the tomogram acquisition parameter processing unit 270 to designate imaging contents designate a scanning method including a tomogram acquisition part and position, the spatial range of a tomogram, a scan line interval, a scan order, a scan speed, and a scan direction.

The fundus movement analysis unit 271 analyzes the broad image acquired by the broad image acquisition unit 220 and calculates information about a small involuntary eye movement (the direction of drift, the moving range of drift and tremors, and the interval and instant of flicks). The fundus movement analysis unit 271 transmits the analysis result to the tomogram acquisition parameter setting unit 272, display unit 260, and data storage unit 250. Note that detailed contents of processing of analyzing the fundus movement will be described later more specifically. In this embodiment, an example will be explained in which fundus movement information is acquired by analyzing a broad fundus image. However, the method of obtaining fundus movement information is not limited to this. For example, a fundus movement may be estimated by analyzing an image obtained by imaging the anterior segment (cornea, pupil, and iris). Alternatively, a fundus movement may be estimated using an eye movement detection method known for an eye-gaze input apparatus.

Based on the target eye information acquired by the target eye information acquisition unit 210, the instruction information acquired by the instruction acquisition unit 240, and the fundus movement information obtained from the fundus movement analysis unit 271, the tomogram acquisition parameter setting unit 272 sets parameters (tomographic imaging parameters) associated with tomogram acquisition so as to minimize the influence of a fundus movement (small involuntary eye movement) on an obtained image. Note that detailed contents of processing of setting the tomographic imaging parameters based on the result from the fundus movement analysis unit 271 will be described later more specifically.

The tomogram acquisition parameter processing unit 270 transmits the set imaging parameters to the tomogram acquisition unit 230, display unit 260, and data storage unit 250.

(Data Storage Unit 250)

The data storage unit 250 stores various kinds of input information in the magnetic disk 102 in association with each other as the data of a patient. More specifically, the data storage unit 250 stores the target eye information input from the target eye information acquisition unit 210, the broad image input from the broad image acquisition unit 220, the tomographic imaging parameters input from the tomogram acquisition parameter processing unit 270, and the tomogram input from the tomogram acquisition unit 230. The data may be stored in an external server (not shown). In this case, the data storage unit 250 transmits the data to the external server.

(Display Unit 260)

The display unit 260 displays, on the monitor 105, the broad image acquired by the broad image acquisition unit 220 or the tomogram obtained by the tomogram acquisition unit 230. The display unit 260 also displays the tomographic imaging parameters set by the tomogram acquisition parameter processing unit 270. If no tomogram can be acquired, information representing it is displayed. A broad fundus image may be displayed together to confirm the traversal scan order, scan direction, scan speed, and imaging position and range.

Figure 3:
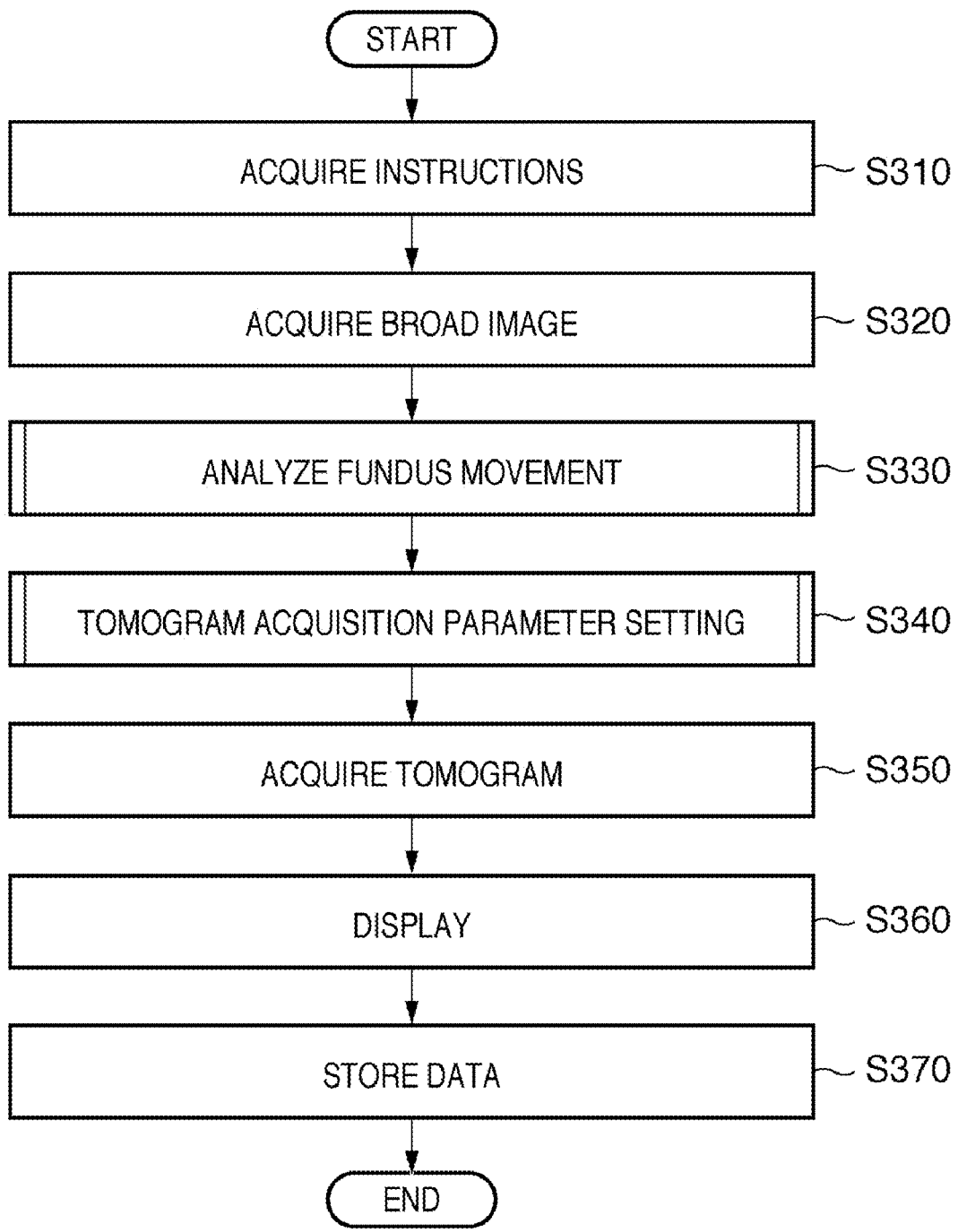
FIG. 3 is a flowchart illustrating the processing procedure of the control apparatus 1 of the tomographic fundus imaging apparatus according to the first embodiment.

A detailed processing procedure executed by the control apparatus 1 of the tomographic fundus imaging apparatus according to this embodiment will be described next with reference to FIG. 3. Note that the functions of the units of the control apparatus 1 according to this embodiment are implemented by causing the CPU 100 to execute a program for implementing the functions of the units and control the overall computer. Prior to the processing to be explained below, program codes complying with the flowchart are already loaded from, for example, the magnetic disk 102 to the main memory 101.

(Process in Step S310)

In step S310, the instruction acquisition unit 240 acquires imaging instruction information for the fundus of a target eye. The instruction acquisition unit externally acquires, as imaging instructions, for example, the designations of the part, position, and imaging range on the fundus of the broad image or tomogram acquisition target. The operator inputs these instructions via the mouse 106 or the keyboard 107. The obtained instructions are transmitted to the broad image acquisition unit 220, tomogram acquisition parameter processing unit 270, and data storage unit 250.

(Process in Step S320)

In step S320, the broad image acquisition unit 220 requests the broad imaging apparatus 2 to capture and transmit a broad image and acquires a broad eye image transmitted from the broad imaging apparatus 2. The broad image acquisition unit 220 transmits the acquired broad image to the fundus movement analysis unit 271, display unit 260, and data storage unit 250.

In step S320, details of settings concerning parameters (the number of images and the shutter speed) of broad image acquisition will be described later.

(Process in Step S330)

In step S330, the fundus movement analysis unit 271 performs image processing of the broad image acquired in step S320 and detects information about a fundus movement. The fundus movement analysis unit 271 of this embodiment detects, as the fundus movement, the momentum and direction of the involuntary small eye movement. The momentum and direction of the involuntary small eye movement are detected by analyzing a motion blur of the broad image acquired in step S320 or detecting the optical flow of the broad image. Detailed contents of each processing will be described later more specifically.

(Process in Step S340)

In step S340, the tomogram acquisition parameter setting unit 272 sets the direction and speed of traversal scan for tomogram acquisition based on the fundus movement information detected in step S330. Based on the instruction information acquired in step 310, the tomogram acquisition parameter setting unit 272 also sets parameters to designate the contents of tomographic imaging. Examples of the parameters are the position and range of tomographic imaging on the fundus. The result is transmitted to the tomogram acquisition unit 230, display unit 260, and data storage unit 250. To reduce the influence of a small involuntary eye movement on the tomographic imaging, the tomographic imaging time is set based on the moving amount of the small involuntary eye movement, and the traversal scan direction of a tomogram is set based on the moving direction information of the small involuntary eye movement. Detailed contents of each setting processing will be described later more specifically.

(Process in Step S350)

In step S350, the tomogram acquisition unit 230 acquires a tomogram from the tomographic imaging apparatus 3 based on the tomographic imaging parameters set in step S340. More specifically, the tomogram acquisition unit 230 transmits a tomographic imaging request to the tomographic imaging apparatus 3 together with the parameters to designate the imaging contents. The tomogram acquisition unit 230 then acquires a tomogram transmitted from the tomographic imaging apparatus 3. The tomogram acquisition unit 230 transmits the acquired tomogram to the display unit 260 and the data storage unit 250. Note that if imaging at a plurality of positions is instructed in step S340, the tomogram acquisition unit 230 transmits imaging requests using the respective imaging parameters to the tomographic imaging apparatus 3 to execute imaging a plurality of number of times.

(Process in Step S360)

Figure 8:
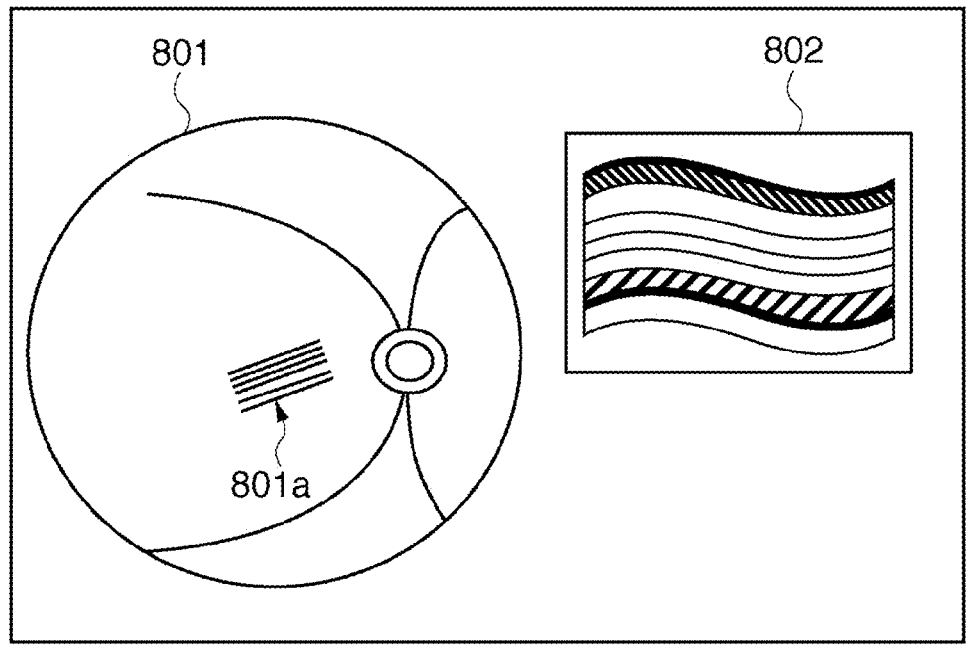
FIG. 8 is a view showing an example of displaying a broad image and a tomogram acquisition range together according to the first embodiment.

In step S360, the display unit 260 displays, the monitor 105, the tomogram obtained in step S350. At this time, the broad image and the tomogram acquisition range on it may be presented together for the purpose of, for example, confirming the imaging part. In addition, the tomographic imaging parameters may be displayed together. FIG. 8 shows a display example. In this example, a broad image 801 and a tomogram acquisition range 801a are displayed on the left side, and an acquired tomogram 802 is displayed on the right side. The tomogram acquisition range 801a also indicates the traversal scan direction and the interval of the imaging positions of a plurality of tomograms.

(Process in Step S370)

In step S370, the data storage unit 250 stores, in the magnetic disk 102, the various kinds of information input in the above-described steps in association with each other as the data of a patient. More specifically, the data storage unit 250 stores the imaging instruction information acquired in step S310, the broad image obtained in step S320, the fundus movement analysis result obtained in step S330, the tomographic imaging parameters obtained in step S340, and the tomogram obtained in step S3350. All the data need not always be stored, as a matter of course.

Note that the data may be stored in an external server (not shown). In this case, the data storage unit 250 transmits the data to the external server.

(Fundus Movement Analysis Processing)

Figure 9:
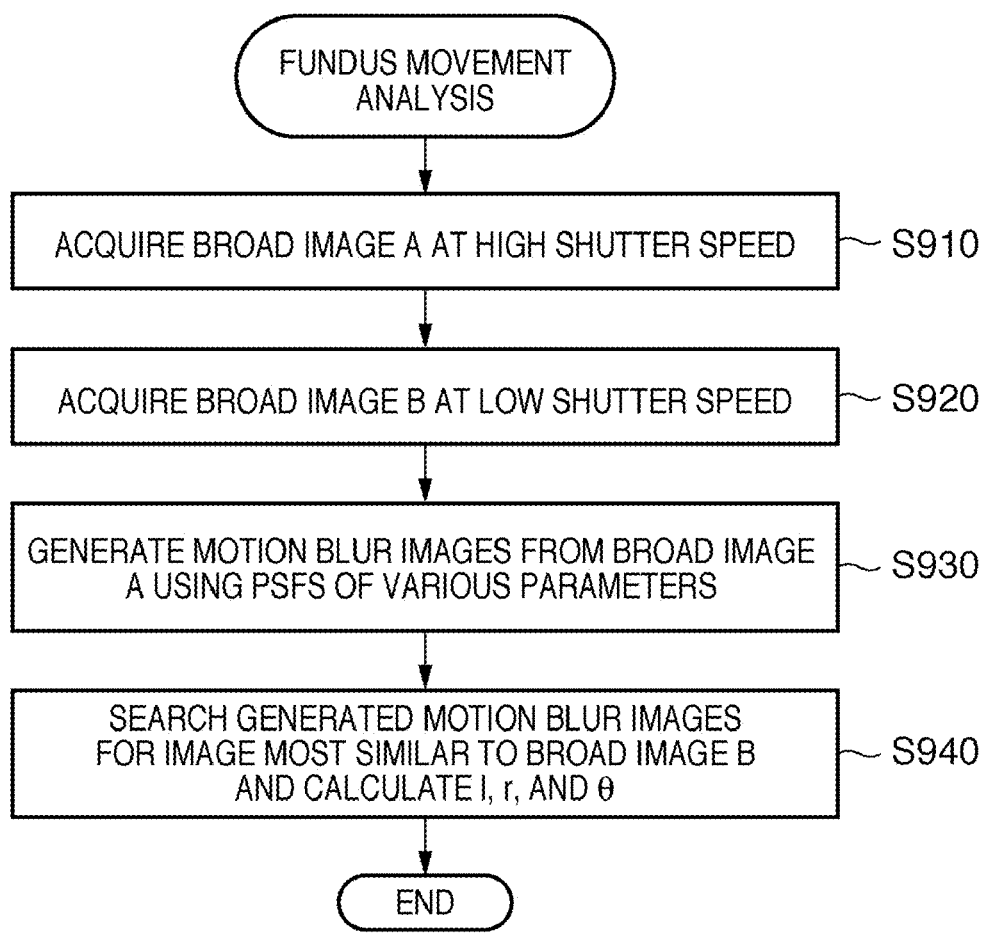
FIG. 9 is a flowchart illustrating the processing procedure of fundus movement analysis according to the first embodiment.

The procedure of fundus movement analysis processing executed in step S330 will be described next with reference to FIG. 9. In this embodiment, a fundus movement is estimated using the property that an object movement at the time of imaging leads to a blur or defocus (motion blur) of a captured image. To do this, the momentum and direction of a fundus movement are estimated using two broad images at different shutter speeds.

In this embodiment, a PSF (Point Spread Function) is used as the image generation model of a defocus (motion blur) in a broad image B caused by a fundus movement to estimate the PSF parameters, thereby estimating the momentum and direction of the motion blur.

An image g(x,y) containing a motion blur is modeled as the convolution integral of a blur-free image f(x,y) and a PSF p(x,y).

$$g(x,y)=f(x,y)*p(x,y)$$

The fundus movement includes not only a movement in one direction but also directional movements (drift and flicks) and also non-directional movements (tremors). Hence, the defocus in the broad image B can be expressed in a plurality of directions (see FIG. 12).

Figure 14:
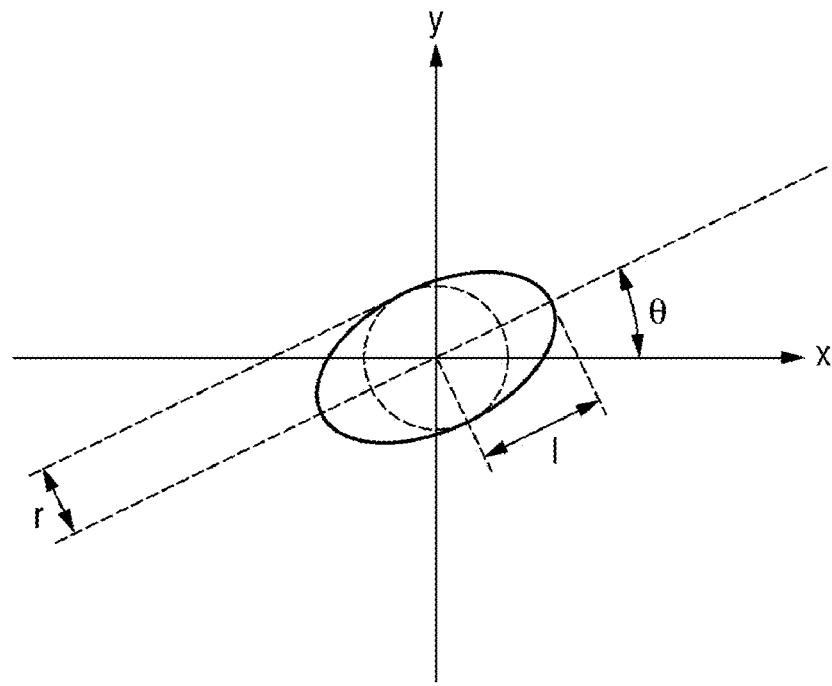
FIG. 14 is a graph for explaining the parameters of a Point Spread Function to model a motion blur according to the first embodiment.

In this embodiment, the PSF of a motion blur is approximated by the following expression (see FIG. 14). FIG. 14 is a graph for explaining the parameters of the Point Spread Function to model a motion blur.

$$p(x, y; r, l, \theta) = \begin{cases} \frac{1}{\pi(l^2 + r^2)}; & \left(\frac{x'}{l}\right)^2 + \left(\frac{y'}{l}\right)^2 \leq 1, \\ 0; & \text{otherwise} \end{cases}$$

$$\text{for } \begin{pmatrix} x' \\ y' \end{pmatrix} = \begin{pmatrix} \cos\theta & \sin\theta \\ -\sin\theta & \cos\theta \end{pmatrix} \begin{pmatrix} x \\ y \end{pmatrix}$$

[Mathematical 1]

where x and y are the positions from a pixel of interest, r is the magnitude of the motion blur in a direction in which the moving amount is small, and l and θ are the magnitude and direction of the motion blur in a direction in which the moving amount is large. In this embodiment, r, l, and θ are used as the PSF parameters.

To estimate the parameters r, l, and θ of the PSF, an image without a motion blur and an image containing a motion blur are obtained. Motion blur images are generated from the image without a motion blur using various values of the parameters r, l, and θ. The generated motion blur images are searched for an image most similar to the captured motion blur image. The PSF parameters of the generated similar image are used as the PSF parameters of the captured motion blur image.

(Process in Step S910)

In step S910, a fundus image at a high shutter speed is acquired from the broad imaging apparatus 2 via the broad image acquisition unit 220. To avoid a blur caused by a flick and drift having a large momentum out of the small involuntary eye movement, the shutter speed is set in, for example, seconds. This shutter speed is not sufficient for avoiding the influence of tremors because a tremor has a frequency of 30 to 100 Hz, as described above. However, the momentum of a tremor itself is smaller than those of the flicks and drift. Hence, tremors are neglected in this embodiment. A higher shutter speed may be set to avoid the influence of tremors. Any shutter speed capable of avoiding flicks and drift is usable even if it is not in seconds as will be described here, and the embodiment is not limited to this. Reference numeral 1010 in FIG. 10 represents an example of a broad image at a high shutter speed. The broad image captured at a high shutter speed will be referred to as a "broad image A" hereinafter.

(Process in Step S920)

In step S920, a fundus image at a low shutter speed is acquired from the broad imaging apparatus 2 via the broad image acquisition unit 220. To obtain a broad image containing the momentum of a small involuntary eye movement as a blur, the shutter speed is set in, for example, seconds. Regarding the small involuntary eye movement, the fundus sometimes moves in a moving width of 0.1 to 0.5 mm per sec. When capturing an image of 1024×1024 pixels in a 15 mm×15 mm fundus region, the fundus moves by 7 to 35 pixels on the image at the shutter speed in seconds and causes defocus in that width. The broad image size, imaging region, and shutter speed are not limited to the above-described examples, as a matter of course. Any values different from those of the embodiment can be adopted as far as the fundus movement appears as a blur in the captured image. Reference numeral 1020 in FIG. 10 represents an example of a broad image at a low shutter speed. The broad image captured at a low shutter speed will be referred to as the "broad image B" hereinafter.

(Process in Step S930)

In step S930, the broad image A free from (or with a few) motion blurs is defined as f(x,y), and convolution processing is performed based on the PSF p(x,y) using various parameters r, l, and θ, as described above. The motion blur images g(x,y) of the respective parameters r, l, and θ are thus generated.

$$g(x,y)=f(x,y)*p(x,y)$$

For the parameter θ, the slope is important but no direction information is used. Hence, an image is generated within the range of π>θ>0.

In addition, an image is generated within the range of $m_{max} \geq l \geq r \geq m_{min}$. The values $m_{max}$ and $m_{min}$ can be either values obtained from the instruction acquisition unit 240 or values stored in the data storage unit 250 in advance.

Needless to say, the convolution processing need not always be executed for the entire broad image A. The processing may be executed for a partial region of interest in the broad image A, for example, a region designated by an operator instruction acquired by the instruction acquisition unit 240 or a region to be subjected to tomographic imaging.

(Process in Step S940)

In step S940, the PSF images of various parameters r, l, and θ generated from the broad image A are compared with the broad image B, thereby searching for an image most similar to the broad image B.

In this embodiment, to measure the similarity, a description will be made using an SSD (Sum of Square Differences).

$$SSD = \frac{1}{N} \sum (A(x) - B(x))^2 \qquad \text{[Mathematical 2]}$$

The captured broad image B is searched for a portion (position x where the SSD is minimized) that is most similar to the reproduced motion blur image in the region of interest.

While comparing with the generated PSF images of the parameters r, l, and θ, the minimum SSDs of the respective images are searched for a minimum SSD. The parameters r, l, and θ of the generated motion blur image at this time are defined as the motion blur parameters.

In this embodiment, a fixed broad image capturing time will be exemplified for the descriptive convenience. However, the time may be changed depending on the target eye information obtained from the target eye information acquisition unit 210. For example, the amount of a patient's fundus movement is known to increase with advancing years. For more accurate analysis, broad images may be captured in a plurality of imaging times and analyzed.

In the above embodiment, the method of estimating the momentum and direction of a fundus movement using PSFs having various parameters has been described. However, the embodiment is not limited to this.

For example, Fourier transform of the equation g(x,y)=f(x,y)*p(x,y) yields G(u,v)=F(u,v) P(U,V). G(u,v) represents the Fourier transform of the broad image B; F(u,v); the Fourier transform of the broad image B; and p(x,y), the Fourier transform of the PSF. P(U,V) is obtained from G(u,v) and F(u,v). Additionally, p(x,y) can be obtained from P(U,V). The parameters r, l, and θ are thus obtained. Alternatively, non-patent reference 1 or 2 presents a motion blur estimation method using a Point Spread Function in detail.

As a method capable of estimating motion blur parameters from one broad image, a method of estimating the momentum and direction of a motion blur by analyzing the Fourier space of an image is presented in non-patent reference 3.

The process in step S330 is executed in the above-described way.

(Tomogram Acquisition Parameter Setting Processing)

Figure 11:
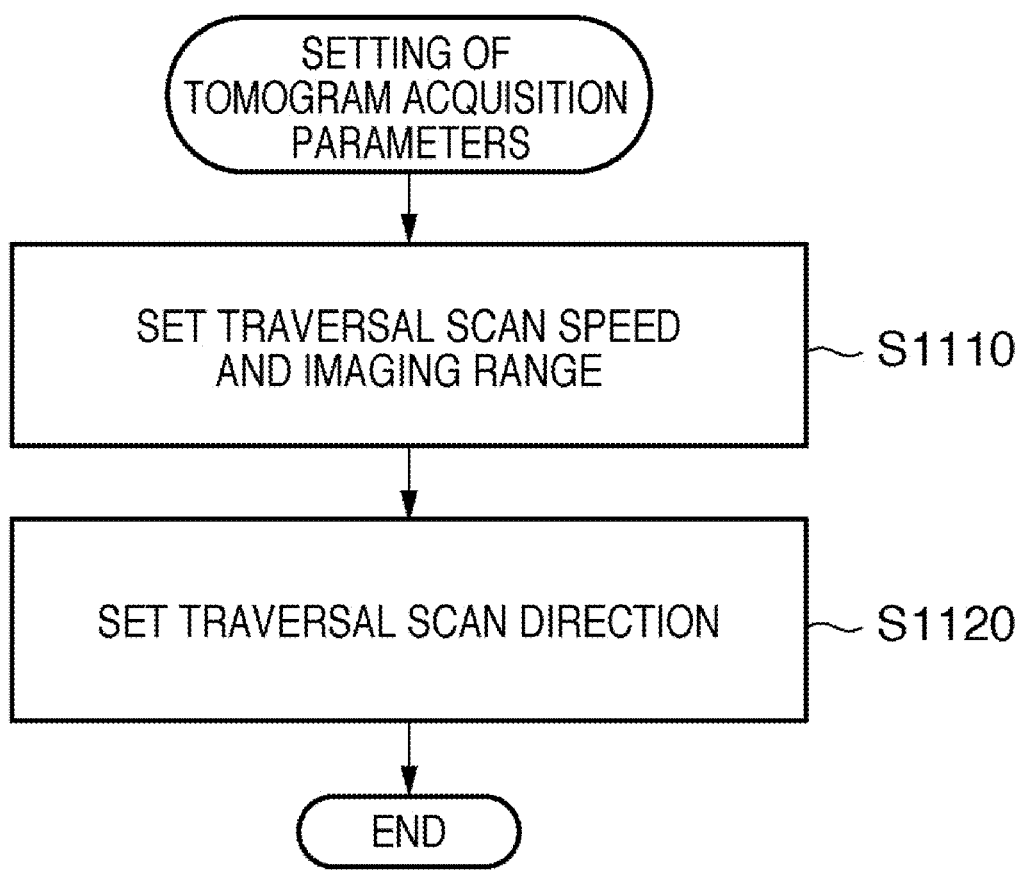
FIG. 11 is a flowchart illustrating the processing procedure of imaging parameter setting according to the first embodiment.

The procedure of tomogram acquisition parameter setting processing executed in step S340 will be described next with reference to FIG. 11.

In step S340, the tomographic imaging time and the traversal scan direction of tomographic imaging are set based on the fundus movement estimation result obtained in step S330.

(Step S1110)

In step S1110, based on the fundus momentum estimation result obtained in step S340, the tomographic imaging time is decided, and additionally, the traversal scan speed and the imaging range are set. When the momentum is large, a tomogram needs to be captured in a shorter time to reduce the influence on tomographic imaging. Conversely, when the momentum is small, its influence on tomographic imaging is expected to be small, and a tomogram can be captured in a longer time.

The A scan acquisition capability speed of the tomographic imaging apparatus 3 is assumed to be 40,000 A Scan/sec for the descriptive convenience. To capture 128 tomograms each having a 512-pixel width in a 6×4 mm region on a fundus surface (retina), an imaging time=(512*128)/400000=1.64 sec is necessary. The size per pixel in the traversal scan direction is 11.72 μm. In this case, the traversal scan speed is 468 mm/sec with respect to the still fundus surface.

In this example, the interval between the continuously captured tomograms is 31.5 μm if the fundus remains still. However, the interval may shift due to the influence of the fundus movement. The (minimum) time from the start of capturing one tomogram to the start of capturing the next tomogram is 12.8 ms. For this reason, if the estimation result obtained in step S330 indicates that the fundus should move by 250 μm per sec, the relative positional shift between two tomograms is 6.4 μm. The error from the expected interval is about 20%.

To decrease the error, the imaging time is shortened. Assume that the imaging time of the same imaging region is halved (imaging time=0.82 sec), and the traversal scan speed is increased. Since the traversal scan speed doubles (936 mm/sec), 128 tomograms each having a 256-pixel width can be captured in the imaging region. The time interval between tomograms changes to 6.4 ms. The relative positional shift between the tomograms decreases to 3.2 μm if the fundus momentum does not change. However, the size per pixel in the traversal scan direction increases to 23.44 μm.

The error to calculate the imaging time may be either a value obtained from the instruction acquisition unit 240 or a parameter decided and stored in the data storage unit 250 in advance. In the above-described embodiment, the imaging time is halved for the sake of convenience. However, based on the tomographic imaging region, the number of tomograms, the fundus momentum, and the designated error, the imaging time can be simplified by $$t = E\left(\frac{m}{(s-l)v}\right) \qquad \text{[Mathematical 3]}$$

where t is the imaging time,
E is the error, $$\frac{m}{(s-l)}$$

is the distance between tomograms, and
v is the estimated fundus movement speed

In the above-described method, an example has been explained in which not the imaging region but the traversal scan speed is changed (i.e., the sampling density (sampling period) is decreased). Instead, not the sampling density (sampling period) but the imaging region may be reduced. To halve the error as in the above-described example, the imaging region may be halved (3×2 mm) at the same traversal scan speed. In this case, which one of the tomogram region and the sampling density (sampling period) should be given priority can be either determined based on the purpose of examination (e.g., medical examination or close examination) obtained from the instruction acquisition unit 240 or designated directly by the operator. For example, in medical examination, it is preferable to examine a wide range. It is therefore possible to give priority to the region and decrease the sampling density (sampling period).

(Process in Step S1120)

Figure 12:
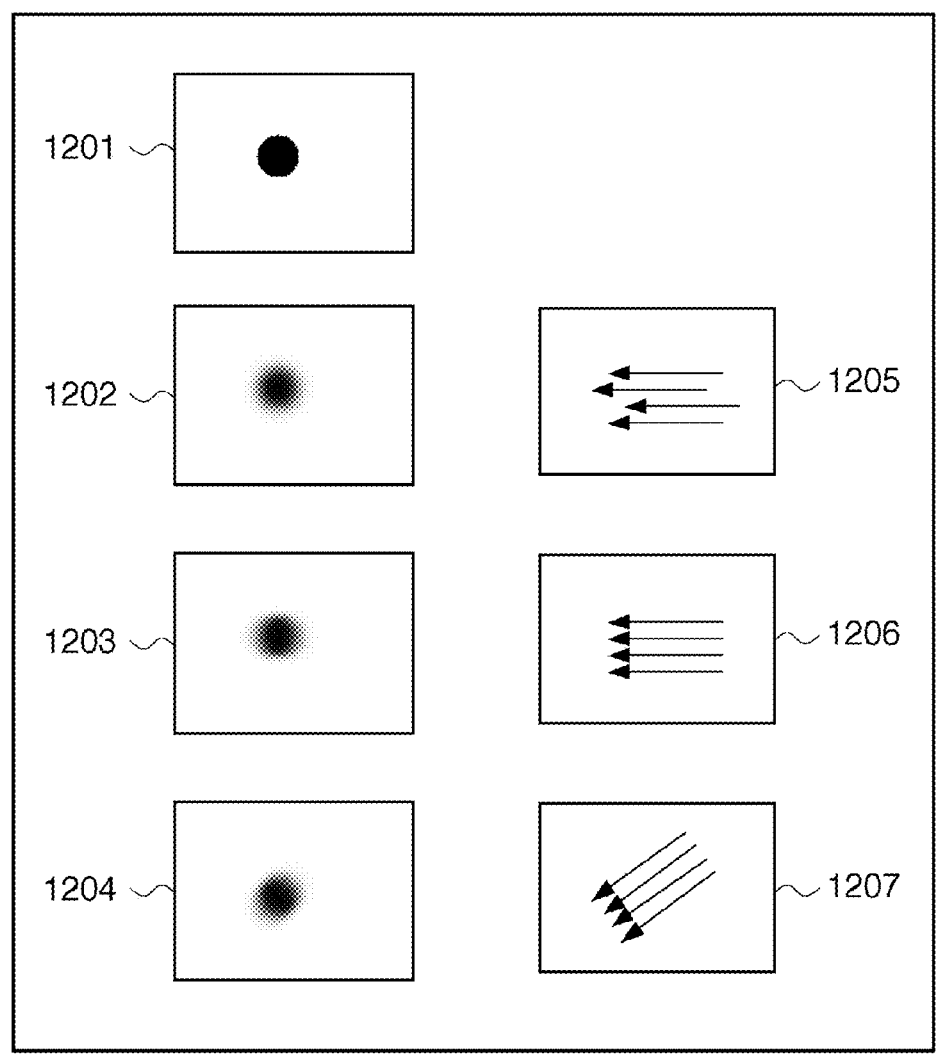
FIG. 12 is a view showing the relationship between a fundus movement direction and a traversal scan direction according to the first embodiment.

In step S1120, the traversal scan direction can be decided based on the fundus movement direction obtained in step S340. FIG. 12 is a view showing the relationship between the fundus movement direction and the traversal scan direction. Referring to FIG. 12, 1201 represents an example of the broad image A captured at a high shutter speed; and 1202, an example of the broad image B captured at a low shutter speed. The influence of the small involuntary eye movement defocuses the outline. However, the defocusing manner is the same in all directions so no directivity is observed. An example of the broad image B indicated by 1203 in FIG. 12 exhibits a strong defocus in the horizontal direction. The broad image B indicated by 1204 in FIG. 12 exhibits a strong defocus in a 45° direction.

When continuously capturing a plurality of tomograms, the relative positional shift between the tomograms needs to be made as small as possible. For this purpose, main scan of tomographic imaging is done in the same direction as the fundus movement direction. Referring to FIG. 12, 1206 indicates a traversal scan direction for the movement 1203; and 1207, a traversal scan direction for the movement 1204.

In this case, although the start position shift between tomograms becomes large, as indicated by 1205 in FIG. 12, the influence of the relative positional shift between the tomograms can be suppressed. However, a mutual information method or a cross-correlation function is also usable to align the tomograms so as to correct the start position shift between them. The process in step S340 is executed in the above-described way.

As described above, according to this embodiment, the traversal scan direction and speed and the imaging range of tomographic imaging are decided using the analysis result of the image blur amount and direction of a broad fundus image. This enables to obtain a tomogram less affected by the fundus movement.

Second Embodiment

In the first embodiment, the fundus movement analysis unit 271 executes the analysis process in step S330 based on the image blur (motion blur) of the broad image B. However, the present invention is not limited to this. In the second embodiment, a fundus movement is analyzed based on the optical flow of broad images. The procedure of processing of a fundus movement analysis unit 271 will be described below.

The fundus movement analysis unit 271 acquires the region information of a fundus as the tomographic imaging target from an instruction acquisition unit 240.

The fundus movement analysis unit 271 acquires, from a broad image acquisition unit 220, a plurality of continuous broad images of the imaging target area at a time interval. In this case, the shutter speed of imaging is set to be high (e.g., seconds). The imaging time interval is set to 30 images/sec. In this embodiment, an SLO (Scanning Laser Opthalmoscope) may be used as a broad imaging apparatus 2, as described above.

In step 330, the optical flow between the broad images is calculated. To do this, a region of interest (e.g., 128×128 pixels) is defined in the broad image, and the same pattern is detected from an adjacent frame by, for example, pattern matching. Pattern matching may be performed using an SSD (Sum of Square Differences).

$$SSD = \frac{1}{N}\sum (A(x) - B(x))^2 \qquad [\text{Mathematical 4}]$$

where A and B are the regions of interest of tomograms that are temporally adjacent, x is the pixel position in the region of interest, and N is the total number of pixels in the region of interest In an adjacent tomogram, the pattern of the region of interest, that is, a position where the SSD is minimized is searched for. The moving amount and direction of the corresponding region of interest are equivalent to the momentum and direction of the fundus movement. If the region of interest moves by x×y pixels with respect to the adjacent image as a result of search, an amount l and direction θ of the fundus movement can be calculated by $$l = \sqrt{(x^2 + y^2)} \qquad [\text{Mathematical 5}]$$
$$\theta = arctg\left(\frac{y}{x}\right)$$

Patent reference 5 (Japanese Patent Laid-Open No. 07-107368) describes details of motion flow (motion vector) detection between images.

As described above, according to this embodiment, when continuous images captured at a high shutter speed are obtained from the broad imaging apparatus 2, fundus movement information can be acquired by analyzing the optical flow between the broad images.

Third Embodiment

In the above-described embodiments, the traversal scan direction and speed and the imaging range of tomographic imaging are set by analyzing a fundus movement. In this embodiment, setting of a more appropriate tomographic imaging start time by fundus movement analysis will be described.

As described above, a small involuntary eye movement contains three movements (tremor, drift, and flick).

Tremor: a quick movement which always occurs in a small momentum

Drift: a slow movement which always occurs in a large momentum

Flick: a quick movement which occurs at a time interval in a large momentum

A tremor has a small momentum (momentum change), and its influence on tomographic imaging is relatively small. A drift largely influences tomographic imaging. However, the influence can be reduced by setting the traversal scan speed and direction. Since a flick occurs to cancel the momentum (momentum change) of drift, its influence can also be reduced by setting the traversal scan speed and direction. In this embodiment, tomographic imaging parameter setting to further reduce the influence of flicks will be explained. A flick is a fundus movement that occurs at a time interval within a measurement time for measuring a fundus movement. In this embodiment, the tendency of the time interval of flicks is detected. Upon detecting a flick, tomographic imaging is started. Imaging parameters are set such that tomographic imaging ends before the next flick.

To detect a flick, a fundus movement analysis unit 271 analyzes a broad image acquired by a broad image acquisition unit 220 and calculates the interval and instant of flicks.

For this purpose, a fundus movement is detected from broad images continuously captured for a time, as described above. When the motion flow to an adjacent broad fundus image has instantaneously become larger (than the average), this is detected as a flick. A plurality of flicks are detected while measuring time, thereby calculating the average time interval of flicks.

When the tendency of the time interval has been detected, a tomographic imaging start instruction is sent to the tomographic imaging apparatus via a tomogram acquisition unit 230 in synchronism with the next flick. The imaging time is set to the average time interval of flicks.

In this embodiment, the average time interval is used as the imaging time. However, the reference for setting is not limited to this. A minimum time interval or a time interval distribution may be used as a reference for setting. The time interval may be set based on any other reference such as an operator instruction acquired by an instruction acquisition unit 240.

Figure 15:
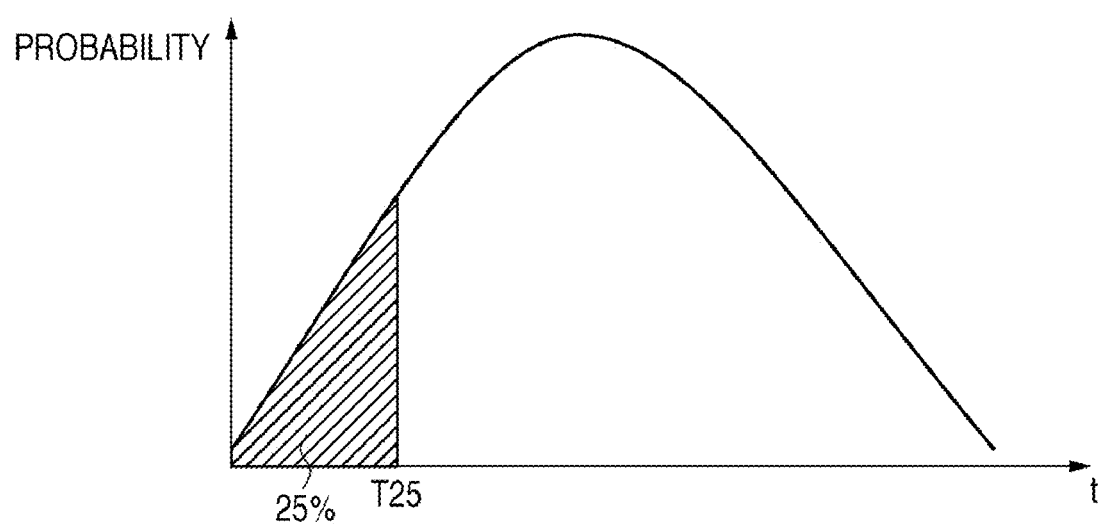
FIG. 15 is a graph showing an example of the probability distribution of flicks according to the third embodiment.

The temporal probability distribution of flicks of the target eye may be obtained, and a time corresponding to, for example, T25 where no flick occurs at a probability of 25% may be set, as shown in FIG. 15. Other than flicks, when the eyelid of the target eye is included in a broad image, the target eye is determined to have winked, and the influence of wink on the tomographic imaging can be reduced in the same way.

As described above, according to this embodiment, a flick or wink information is detected by analyzing continuously captured broad images. This enables to reduce the influence of a flick or wink on a tomogram.

Fourth Embodiment

In the above-described embodiments, tomogram parameters are set by analyzing a fundus movement. However, it is sometimes difficult to appropriately set tomogram parameters based on a fundus movement. In this embodiment, an arrangement for outputting a notification, that is, a warning if the conditions of tomogram parameters are not satisfied will be described.

Figure 13:
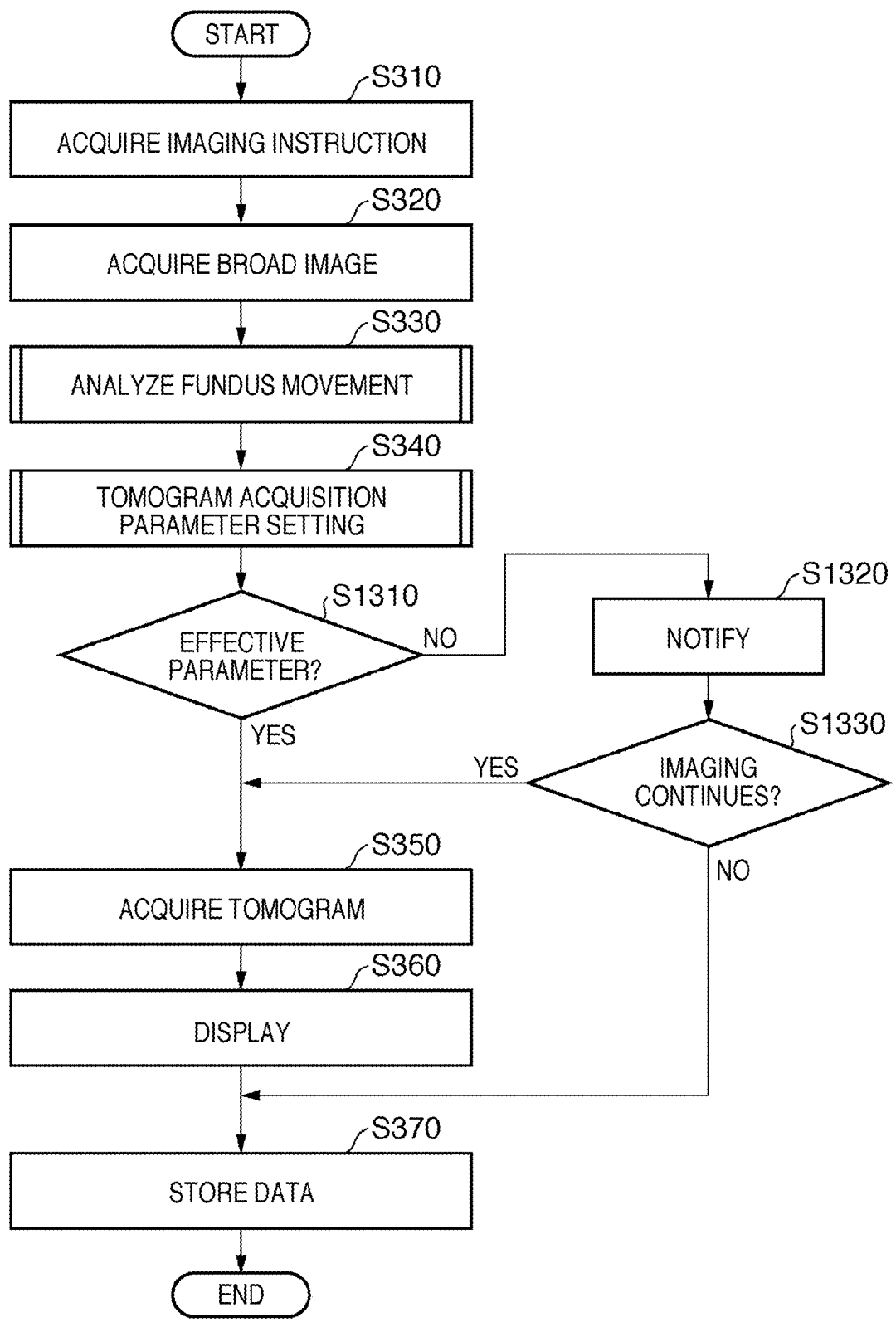
FIG. 13 is a flowchart illustrating the processing procedure of a control apparatus 1 of a tomographic fundus imaging apparatus according to the fourth embodiment.

A detailed processing procedure to be executed by a control apparatus 1 of a tomographic fundus imaging apparatus according to this embodiment will be explained with reference to FIG. 13. Note that a description of steps common to those of the already described processing procedure in FIG. 3 will be omitted.

(Process in Step S1310)

In step S1310, tomogram acquisition parameters set in step S340 are confirmed to determine whether they are effective parameters that satisfy the conditions. As the conditions, imaging instructions obtained in step S310 are usable. The imaging instructions include an imaging range.

Upon confirming tomogram acquisition parameters set in step S340 (S1310) and determining that they are effective parameters, the process advances to step S350 to acquire a tomogram.

On the other hand, if the imaging range decreases to, for example, ½ or ¾, the parameters are determined to be ineffective, and the process advances to step S1320. In step S1320, a display unit 260 displays a warning representing that the tomogram acquisition parameters set in step S340 are not effective. The warning can be done not only by displaying a warning message on a monitor 105 of the display unit 260 but also by, for example, turning on a warning lamp or making a buzzer sound. The criterion of determination is not limited to setting of a parameter to reduce the imaging range to ½ or ¾. Any other condition is usable. As another example of the condition for warning output, when the fundus movement is too large, the imaging time needs to be extremely short. In this case, however, the number of samples is too small, and no effective tomogram can be obtained.

In step S1330, the imaging instructor is required to confirm whether to continue imaging.

In step S1330, it is determined based on an input from the imaging instructor whether to continue imaging. To continue imaging, the process advances to step S350 to acquire a tomogram. If imaging should not continue, the process advances to step 370 to store necessary information, and the overall processing ends.

As described above, according to this embodiment, if it is impossible to obtain an effective tomogram acquisition parameter, a warning is output to request determination of the imaging instructor. If imaging should not continue, acquisition of ineffective tomograms can be avoided.

Other Embodiments

The present invention is also implemented by executing the following processing. That is, the processing is executed by supplying software (program) for implementing the functions of the above-described embodiments to a system or apparatus via a network or various kinds of storage media and causing the computer (or CPU or MPU) of the system or apparatus to read out and execute the program.

The present invention is not limited to the above embodiments, and various changes and modifications can be made within the spirit and scope of the present invention. Therefore, to apprise the public of the scope of the present invention, the following claims are made.

This application claims the benefit of Japanese Patent Application No. 2008-271439, filed Oct. 21, 2008, which is hereby incorporated by reference herein in its entirety.

The invention claimed is:

1. An imaging control apparatus which controls an imaging unit adapted to scan a fundus of a target eye to capture a tomogram of the fundus, comprising:
    an acquisition unit adapted to acquire information indicating a movement of the fundus which moves in a plurality of directions in a predetermined time interval;
    an analysis unit adapted to analyze the information acquired by said acquisition unit, and acquire a direction representing the plurality of directions based on a magnitude of each directional component of the movement of the fundus; and
    a control unit adapted to control the imaging unit so as to align a direction of main scan of the imaging unit with the direction acquired based on an analysis result of said analysis unit.

2. The imaging control apparatus according to claim 1, wherein to align the direction of main scan of the imaging unit with the direction of the fundus movement, said control unit controls at least one of an imaging range of the imaging unit, a scan speed of the imaging unit within the imaging range, a sampling period of imaging of the imaging unit, and an imaging position at which the unit starts imaging.

3. The imaging control apparatus according to claim 1, wherein
    said acquisition unit further acquires information representing a change in a momentum of the fundus movement within a measurement time for measuring the fundus movement, and
    said control unit controls to cause the imaging unit to start imaging in response to acquisition of the information representing the change in the momentum.

4. The imaging control apparatus according to claim 1, further comprising a setting unit adapted to receive setting of an imaging parameter to obtain the tomogram of the fundus,
    wherein said acquisition unit acquires the information representing the direction of the fundus movement based on the imaging parameter received by said setting unit.

5. The imaging control apparatus according to claim 4, further comprising a warning unit adapted to output a warning to notify that it is impossible to capture the tomogram of the fundus,
    wherein said analysis unit determines, based on the analysis result of the direction of the fundus movement, whether it is possible to capture the tomogram of the fundus using the imaging parameter, and if said analysis unit has determined that it is impossible to capture the tomogram of the fundus using the imaging parameter, said warning unit outputs the warning.

6. The imaging control apparatus according to claim 1, further comprising a broad image acquisition unit adapted to acquire a broad image of the fundus of the target eye, wherein said acquisition unit acquires the information representing the direction of the fundus movement based on image processing of the broad image of the fundus.

7. The imaging control apparatus according to claim 6, wherein the acquisition unit acquires the information representing the direction of fundus movement of the eye based on a first broad image captured at a first shutter speed and a second broad image captured at second shutter speed that is lower than the first shutter speed, and wherein the analysis unit analyzes the direction of fundus movement by generating motion blur images from the first broad image and comparing the motion blur images to the second broad image.

8. The imaging control apparatus according to claim 6, wherein the acquisition unit acquires information representing the direction of fundus movement of the eye based on a plurality of broad images of the fundus captured in a predetermined time interval, and wherein the analysis unit analyzes the direction of fundus movement by determining the optical flow between the plurality of broad images.

9. An imaging apparatus comprising an imaging control apparatus of claim 1.

10. The apparatus according to claim 1, wherein the acquisition unit acquires a plurality of tomograms of the fundus to be acquired by the imaging unit as the information representing the movement of the fundus.

11. An imaging control method of an imaging control apparatus which controls an imaging unit adapted to scan a fundus of a target eye to capture a tomogram of the fundus, comprising:

an acquisition step of acquiring information indicating a movement of the fundus which moves in a plurality of directions in a predetermined time interval;

an analysis step of analyzing the information acquired in the acquisition step, and acquiring a direction representing the plurality of directions based on a magnitude of each directional component of the movement of the fundus; and a control step of controlling the imaging unit so as to align a direction of main scan of the imaging unit with the direction acquired based on an analysis result in the analysis step.

12. The imaging control method according to claim 11, wherein in the control step, to align the direction of main scan of the imaging unit with the direction of the fundus movement, at least one of an imaging range of the imaging unit, a scan speed of the imaging unit within the imaging range, a sampling period of imaging of the imaging unit, and an imaging position at which the imaging unit starts imaging is controlled.

13. The imaging control method according to claim 11, wherein in the acquisition step, information representing a change in a momentum of the fundus movement is further acquired within a measurement time for measuring the fundus movement, and in the control step, control is performed to cause the imaging unit to start imaging in response to acquisition of the information representing the change in the momentum.

14. The imaging control method according to claim 11, further comprising the setting step of receiving setting of an imaging parameter to obtain the tomogram of the fundus, wherein in the acquisition step, the information representing the direction of the fundus movement is acquired based on the imaging parameter received in the setting step.

15. The imaging control method according to claim 14, further comprising the warning step of outputting a warning to notify that it is impossible to capture the tomogram of the fundus, wherein in the analysis step, it is determined, based on the analysis result of the direction of the fundus movement, whether it is possible to capture the tomogram of the fundus using the imaging parameter, and if it is determined in the analysis step that it is impossible to capture the tomogram of the fundus using the imaging parameter, the warning is output in the warning step.

16. The imaging control method according to claim 11, further comprising the broad image acquisition step of acquiring a broad image of the fundus of the target eye, wherein in the acquisition step, the information representing the direction of the fundus movement is acquired based on image processing of the broad image of the fundus.

17. A program which causes a computer to execute an imaging control method of claim 11.

18. A computer-readable storage medium storing a program of claim 17.

* * * * *